United States Patent
Stengel et al.

(10) Patent No.: US 8,659,756 B2
(45) Date of Patent: Feb. 25, 2014

(54) SCATTERED LIGHT MEASURING METHOD

(75) Inventors: Karl Stengel, Deizisau (DE); Gerhard Haaga, Ohmden (DE); Michael Neuendorf, Plochingen (DE); Raymond Sieg, Esslingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 13/812,598

(22) PCT Filed: Jul. 18, 2011

(86) PCT No.: PCT/EP2011/062267
§ 371 (c)(1),
(2), (4) Date: Apr. 4, 2013

(87) PCT Pub. No.: WO2012/016815
PCT Pub. Date: Feb. 9, 2012

(65) Prior Publication Data
US 2013/0182252 A1 Jul. 18, 2013

(30) Foreign Application Priority Data
Aug. 4, 2010 (DE) .......................... 10 2010 038 897

(51) Int. Cl.
*G01N 15/06* (2006.01)

(52) U.S. Cl.
USPC .......................................... 356/336; 356/341

(58) Field of Classification Search
USPC ................ 356/335–343, 72–73, 244, 246; 250/574–575
See application file for complete search history.

(56) References Cited

U.S. PATENT DOCUMENTS

| 4,420,256 A * | 12/1983 | Fladda et al. ................. 356/336 |
| 4,652,755 A * | 3/1987 | Solomon et al. ........... 250/341.7 |
| 4,679,939 A * | 7/1987 | Curry et al. .................... 356/336 |
| 5,194,921 A * | 3/1993 | Tambo et al. ................. 356/432 |
| 5,777,748 A * | 7/1998 | Stengel .......................... 356/438 |
| 6,181,419 B1 * | 1/2001 | Snelling et al. ............... 356/335 |
| 6,774,994 B1 * | 8/2004 | Wyatt et al. ................... 356/337 |
| 7,782,459 B2 * | 8/2010 | Holve ............................ 356/336 |
| 2004/0233431 A1 * | 11/2004 | Ganz et al. .................... 356/338 |
| 2009/0079981 A1 | 3/2009 | Holve |
| 2012/0293797 A1 * | 11/2012 | Braeckmans et al. ........ 356/246 |

FOREIGN PATENT DOCUMENTS

DE 20 2008 014667 1/2009
GB 2 226 880 7/1990
GB 2 284 050 5/1995

OTHER PUBLICATIONS

International Search Report, dated Sep. 21, 2011, issued in corresponding PCT/EP2011/062267.

* cited by examiner

*Primary Examiner* — Sang Nguyen
(74) *Attorney, Agent, or Firm* — Kenyon & Kenyon LLP

(57) ABSTRACT

A scattered light method for measuring particle-dependent parameters of gases, in particular particle-dependent parameters of internal combustion engine exhaust gases or other colloids, includes introducing a particle-containing gas into a measuring chamber; emitting a light beam into the measuring chamber; receiving light scattered by the particles using at least two scattered light sensors, the scattered light sensors generating scattered light sensor signals, each being a function of the light received by the respective scattered light sensor; determining an average particle size from the scattered light sensor signals from at least two scattered light sensors and determining at least one further particle parameter from the previously determined average particle size and the scattered light sensor signals.

10 Claims, 2 Drawing Sheets

SCATTERED LIGHT MEASURING METHOD

CROSS REFERENCE TO RELATED APPLICATIONS

The present application is the national stage entry of International Patent Application No. PCT/EP2011/062267, filed on Jul. 18, 2011, which claims priority to Application No. DE 10 2010 038 897.1, filed in the Federal Republic of Germany on Aug. 4, 2010.

FIELD OF INVENTION

The present invention relates to a scattered light measuring method for determining at least one particle-dependent parameter of gases, in particular exhaust gases of an internal combustion engine, and a device for carrying out the method according to the present invention.

BACKGROUND INFORMATION

To measure particle-dependent parameters, e.g., a particle mass concentration (mass/volume) in exhaust gases and other colloids, scattered light methods are often used. A light beam is emitted into the gas which contains particles. A laser is often used as the light source. The light (scattered light) scattered by the particles is detected and evaluated by at least two sensors positioned at different angles with respect to the direction of the emitted light beam.

The intensity of the scattered light and thus the values of the signals output by the sensors also depend on the average size of the particles in addition to depending on the particle mass concentration to be measured. Therefore, with an unknown particle size, it is impossible to determine the particle mass concentration from the scattered light sensor signals alone.

SUMMARY

An object of the present invention is to provide a scattered light method which permits an accurate determination of particle-dependent parameters, e.g., the particle mass concentration in a gas, even if the size of the particles is unknown.

This object is achieved by a scattered light method according to the present invention and a device for scattered light measurement of particle-containing gases according to the present invention.

In a scattered light method according to the present invention for measuring and determining particle-dependent parameters of particle-containing (exhaust) gases, the particle-containing gas to be measured is introduced into a measuring chamber. A light beam is emitted into the measuring chamber and is scattered by the particles contained in the gas. The light (scattered light) scattered by the particles is received by at least two scattered light sensors, and the scattered light sensors output electric scattered light sensor signals, each of which is a function of the intensity of the scattered light received by the respective scattered light sensor. The average particle size is determined from the scattered light sensor signals of at least two scattered light sensors using a method known from the related art. With knowledge of the average particle size determined in this way, additional particle-dependent parameters, e.g., the particle mass concentration within the measuring chamber and/or an absorption coefficient of the particle-containing gas may be determined from the scattered light sensor signals.

Using a method according to the present invention, particle-dependent parameters, in particular a particle mass concentration and an absorption coefficient, which is compatible with opacity meters, may be determined with high accuracy, even if the average particle size prior to the measurement is unknown. A method according to the present invention is simple and may be carried out with little effort because traditional scattered-light measuring devices may be used without requiring a mechanical upgrade or retrofit.

The scattered light sensors are preferably situated at various angles with respect to the incident beam direction of the light beam emitted into the measuring chamber, so they detect scattered light which is scattered in various directions by the particles contained in the gas.

In one exemplary embodiment, the average particle size is a polynomial function of at least two scattered light sensor signals. In the related art it is known to determine the particle size from at least two scattered light sensor signals, as described in U.S. Patent Application Publication No. 2009/0079981 A and UK Patent Application No. GB 2 226 880 A, for example.

In one exemplary embodiment, the particle parameters to be determined are polynomial functions of the scattered light sensor signals and a previously determined characteristic curve slope.

The coefficients of the polynomial functions are determinable by theoretical considerations or by adjusting (fitting) the corresponding polynomial function to experimental findings.

Polynomial functions are simple to handle and permit a rapid and accurate calculation of the desired parameters. The accuracy of the method may be selected as needed through the choice of the degree of the polynomial in particular. Polynomial functions may be fitted well to experimental findings using known fitting algorithms.

The present invention also includes a device for scattered light measurement of particle-containing gases using a measuring chamber designed to accommodate the particle-containing gas to be measured; a light source which emits a light beam into the measuring chamber during operation; at least two scattered light sensors, which are situated in the measuring chamber in such a way that they detect light (scattered light) scattered by particles contained in the gas at various angles; and an evaluation device designed to carry out a method according to the present invention for measuring particle parameters in gases.

In one exemplary embodiment, the light source is a monochromatic light source, in particular a laser light source. The scattered light method may be carried out particularly effectively and with high accuracy using a monochromatic light source. A laser light source is particularly suitable for providing high quality monochromatic light.

An exemplary embodiment of the present invention is described below with reference to the accompanying drawings.

DETAILED DESCRIPTION

Figure 1:
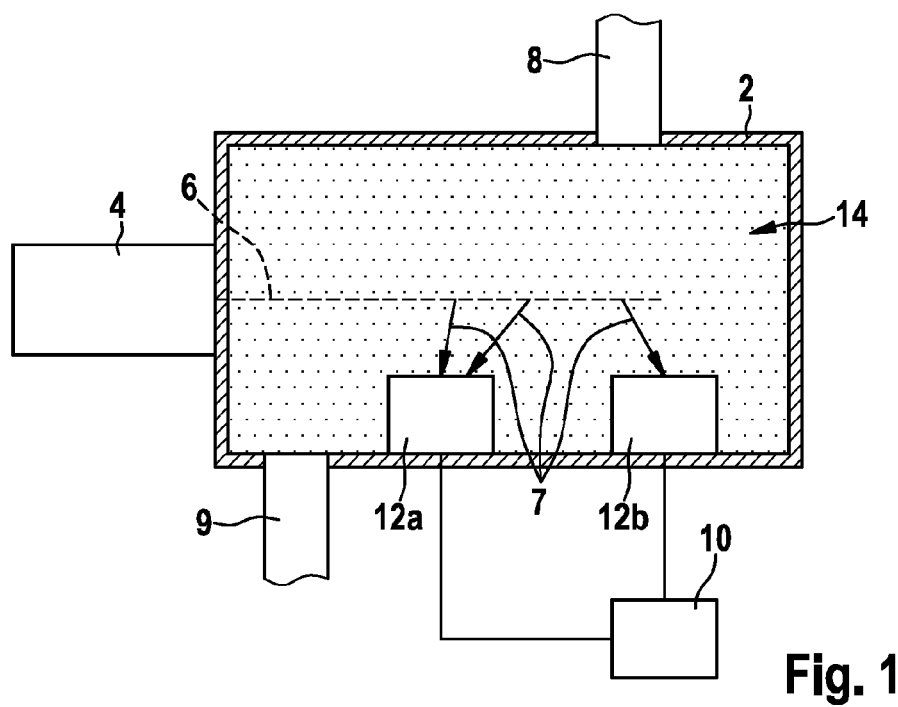
FIG. 1 shows the schematic configuration of a device according to the present invention for scattered light measurement.

A device according to the present invention for scattered light measurement as shown in FIG. 1 has a measuring chamber 2, designed to have at least one inlet line 8 and at least one outlet line 9. During operation, exhaust gas to be measured or some other colloid is passed through measuring chamber 2 via inlet line 8 and outlet line 9.

A light source 4 designed as a laser light source 4, for example, is provided in or on measuring chamber 2. During operation, light source 4 emits a light beam 6 into measuring chamber 2.

In addition, at least two scattered light sensors 12a, 12b are situated in measuring chamber 2. Scattered light sensors 12a, 12b are electrically connected to an evaluation device 10 situated outside of measuring chamber 2 in order to transmit scattered light sensor signals, each of which is a function of scattered light 7 received by respective scattered light sensor 12a, 12b, to evaluation device 10.

During operation, light 6 emitted by light source 4 into measuring chamber 2 is scattered by particles 14 present in the gas introduced into measuring chamber 2. Scattered light 7 is detected by scattered light sensors 12a, 12b, and respective scattered light sensor signals are output to evaluation device 10 by scattered light sensors 12a, 12b.

Figure 2:
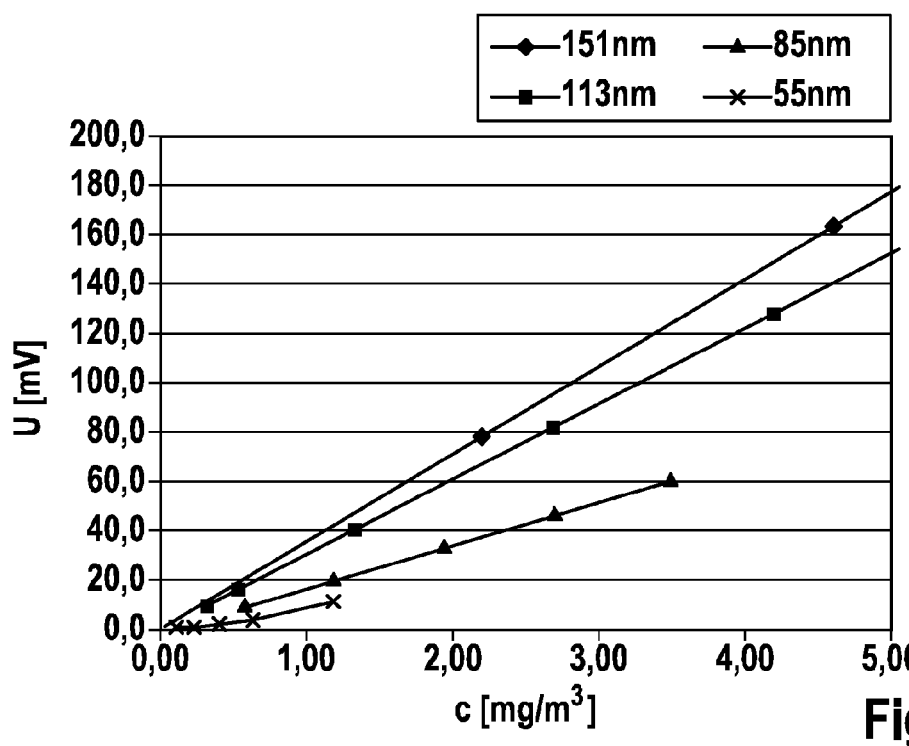
FIG. 2 shows a diagram illustrating the dependence of the scattered light sensor signal on the average particle size and the particle mass concentration.

FIG. 2 shows a diagram illustrating the dependence of electrical voltage U of a scattered light sensor signal output by one of scattered light sensors 12a, 12b as a function of particle mass concentration c in measuring chamber 2 and average particle size d.

FIG. 2 in particular shows voltage U of the scattered light sensor signal (y axis) output by a scattered light sensor 12a, 12b plotted as a function of particle mass concentration c in measuring chamber 2 (x axis) for various average particle sizes d. Various average particle sizes d are represented here by different symbols for the measuring points.

The diagram in FIG. 2 shows clearly that the relationship between particle mass concentration c and scattered light sensor signal U depends to a great extent on average particle size d. It is impossible in particular to deduce particle mass concentration c from the scattered light sensor signal U if average particle size d is not known, because in this case one does not know which of the characteristic lines (straight lines) shown in FIG. 2 is to be used for the evaluation.

Figure 3:
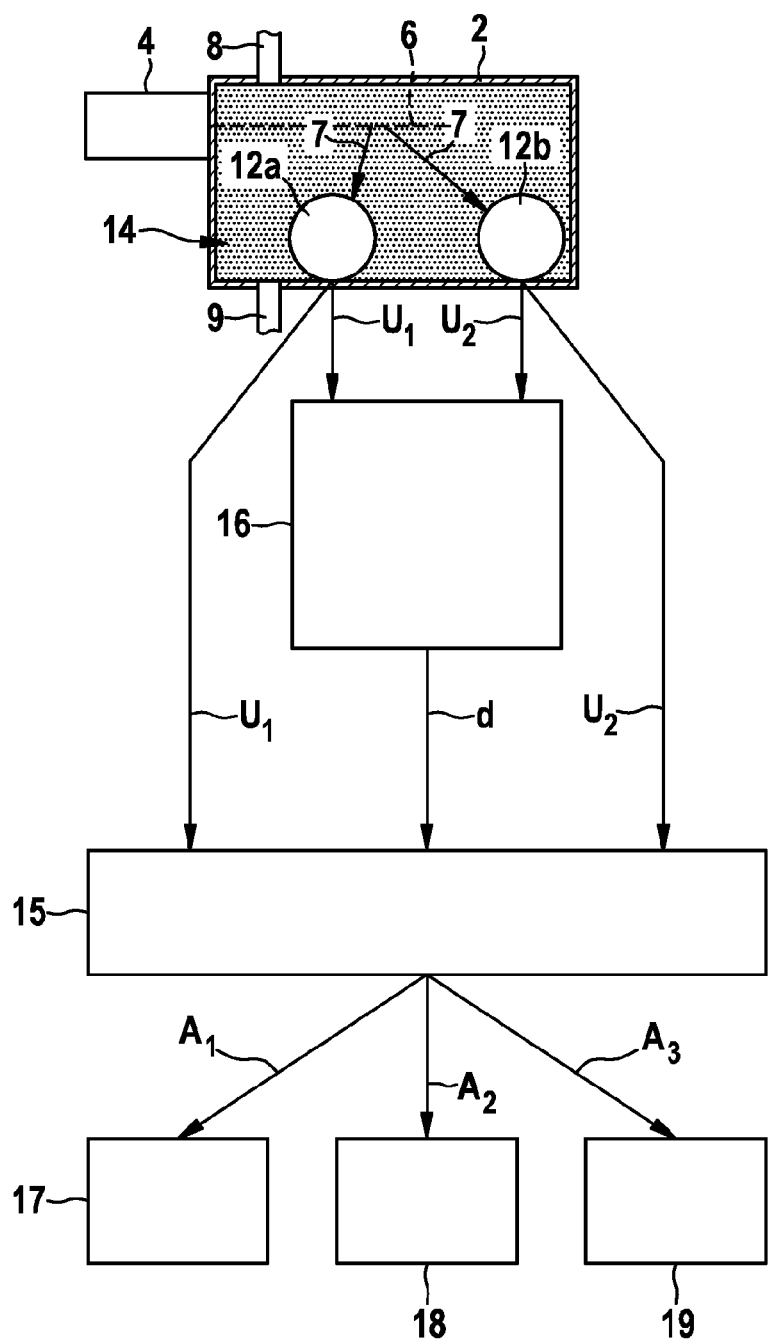
FIG. 3 shows a schematic flow chart of a scattered light measuring method according to the present invention.

FIG. 3 shows a schematic flow chart of a method according to the present invention.

As already described, a light beam 6 is emitted from a light source 4 into a measuring chamber 2, where the gas to be measured is located. Light 7 scattered by particles 14 contained in the gas to be measured is detected by two scattered light sensors 12a, 12b. Scattered light sensors 12a, 12b output scattered light sensor signals $U_1$, $U_2$, which are a function of scattered light 7 received by respective scattered light sensor 12a, 12b.

In a first step 16, average size d of particles 14 contained in the gas inside measuring chamber 2 is calculated from scattered light sensor signals $U_1$, $U_2$ of both scattered light sensors 12a, 12b. Average particle size d of an unknown particle distribution is calculated from at least two scattered light sensor signals $U_1$, $U_2$ as explained above and as is known in the related art.

If average particle size d is known, then a characteristic curve assigned to corresponding average particle size d may be selected from a known characteristics field (see FIG. 2, for example) stored in the evaluation device and to calculate from scattered light sensor signals $U_1$, $U_2$ in step 15 average particle mass concentration c in measuring chamber 2 or other parameters 17, 18, 19 depending on particles 14, e.g., an absorption coefficient, with the aid of this characteristic curve.

In one exemplary embodiment, parameters 17, 18, 19 to be determined in this way are represented in step 15 as functions $h_n$ of scattered light sensor signals $U_1$, $U_2$ and a characteristic curve slope m=g(d), which depends on average particle size d:

$$A_n = h_n(U1, U2, m).$$

Functions g(d), i.e., the characteristic curve slope as a function of average particle size d and $h_n(U1,U2,m)$, may be represented as polynomial functions, the polynomial coefficients being determinable, e.g., by fitting the corresponding polynomial function to experimental measuring results. Alternatively, functions g and $h_n$ may be formulated on the basis of theoretical considerations.

Using a method and a device according to the present invention, it is possible to reliably determine particle mass concentration c and/or other parameters 17, 18, 19 as a function of particles 14 in gases, even when average particle size d is unknown prior to the measurement.

What is claimed is:

1. A scattered light method for determining at least one particle-dependent parameter of particle-containing gases, in particular particle-containing exhaust gases of an internal combustion engine, the method comprising:
   a) introducing a particle-containing gas into a measuring chamber;
   b) emitting a light beam into the measuring chamber;
   c) receiving scattered light, which has been scattered on particles contained in the gas, using at least two scattered light sensors, the scattered light sensors generating scattered light sensor signals, each scattered light sensor signal being a function of the scattered light received by the respective scattered light sensor;
   d) determining, by a processing device, an average particle size from the scattered light sensor signals of the at least two scattered light sensors; and
   e) determining, by the processing device, at least one additional particle parameter from the previously determined average particle size and from the scattered light sensor signals.

2. The method according to claim 1, wherein the scattered light sensors are at least one of embodied and situated such that the sensors detect the scattered light, which has been scattered at different angles with respect to the emitted light beam.

3. The method according to claim 1, wherein a particle-dependent parameter to be determined is one of a mass concentration of the particles within the gas in the measuring chamber and an optical absorption coefficient of the particle-containing gas.

4. The method according to claim 3, wherein a slope of a characteristic curve of the scattered light sensor signals as a function of the mass concentration of the particles is represented as a polynomial function of the average particle size.

5. The method according to claim 4, wherein a particle-dependent parameter to be determined is represented as a polynomial function of the scattered light sensor signals and the slope of the characteristic curve, which depends on the average particle size.

6. The method according to claim 1, wherein the average particle size is represented as a polynomial function of the scattered light sensor signals.

7. A device for determining at least one particle-dependent parameter of particle-containing gases, in particular particle-containing exhaust gases of an internal combustion engine, comprising:

a measuring chamber, which is configured to accommodate a particle-containing gas to be measured;

a light source, which is configured to emit a light beam into the measuring chamber during operation;

at least two scattered light sensors, which are situated in the measuring chamber such that during operation, the at least two scattered light sensors detect scattered light, which has been scattered by particles contained in the gas; and an evaluation device, which is connected to the scattered light sensors for data transmission and is configured to determine an average particle size from the scattered light sensor signals and at least one additional particle-dependent parameter from the previously determined average particle size and from the scattered light sensor signals.

8. The device according to claim 7, wherein the scattered light sensors are situated at least at two different angles in the measuring chamber with respect to a beaming direction of the light beam.

9. The device according to claim 7, wherein the light source is a monochromatic light source.

10. The device according to claim 7, wherein the light source is a laser light source.

* * * * *